(12) United States Patent
Burdette et al.

(10) Patent No.: US 9,649,127 B2
(45) Date of Patent: *May 16, 2017

(54) REAL TIME THREE-DIMENSIONAL HEAT-INDUCED ECHO-STRAIN IMAGING FOR MONITORING HIGH-INTENSITY ACOUSTIC ABLATION PRODUCED BY CONFORMAL INTERSTITIAL AND EXTERNAL DIRECTIONAL ULTRASOUND THERAPY APPLICATORS

(71) Applicants: Acoustic MedSystems, Inc., Savoy, IL (US); The Johns Hopkins University, Baltimore, MD (US)

(72) Inventors: Everette C. Burdette, Savoy, IL (US); Emad M. Boctor, Baltimore, MD (US)

(73) Assignees: ACOUSTIC MEDSYSTEMS, INC., Savoy, IL (US); THE JOHNS HOPKINS UNIVERSITY, Baltimore, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/745,116

(22) Filed: Jun. 19, 2015

(65) Prior Publication Data

US 2016/0015417 A1   Jan. 21, 2016

Related U.S. Application Data

(63) Continuation of application No. 12/712,019, filed on Feb. 24, 2010, now Pat. No. 9,060,670.
(Continued)

(51) Int. Cl.
*A61B 8/00* (2006.01)
*A61B 17/32* (2006.01)
(Continued)

(52) U.S. Cl.
CPC ........ *A61B 17/320068* (2013.01); *A61B 8/00* (2013.01); *A61B 8/085* (2013.01);
(Continued)

(58) Field of Classification Search
CPC ........... A61B 8/00; A61B 8/085; A61B 8/485; A61B 2017/00084; A61B 2017/00106; A61B 2017/320068
See application file for complete search history.

(56) References Cited

U.S. PATENT DOCUMENTS

| 4,576,177 A | 3/1986 | Webster, Jr. |
| 5,759,162 A | 6/1998 | Oppelt et al. |

(Continued)

OTHER PUBLICATIONS

Non-Final Office Action on U.S. Appl. No. 12/712,019 Dated Oct. 27, 2011, 6 pages.
(Continued)

*Primary Examiner* — Peter Luong
(74) *Attorney, Agent, or Firm* — Foley & Lardner LLP

(57) ABSTRACT

A system for thermal treatment or ablation of tissue includes an ultrasonic thermal ablation probe, an ultrasonic three-dimensional imaging probe that captures an image from radio frequency image data obtained before the radio frequency image data is processed, a control system for multi-axis control of the imaging probe's position, and an ultrasonic feedback mechanism that measures ultrasound echo strain to estimate heat-induced structural changes of an area surrounding the ultrasonic thermal ablation probe, from the image. The ultrasonic thermal ablation probe is either an interstitial ablator inserted into tissue, a natural cavity or a vessel to emit high intensity ultrasound energy to deposit thermal dose, or an external applicator that emits a directional high intensity ultrasound energy to deposit thermal dose via surface contact with tissue. The control system adjusts power levels of the ultrasonic thermal ablation probe based on the estimated heat-induced structural changes.

18 Claims, 14 Drawing Sheets

Related U.S. Application Data

(60) Provisional application No. 61/155,080, filed on Feb. 24, 2009.

(51) Int. Cl.

| | | |
|---|---|---|
| *A61B 8/08* | (2006.01) | |
| *A61N 7/02* | (2006.01) | |
| *A61B 17/00* | (2006.01) | |
| *A61N 7/00* | (2006.01) | |
| *A61B 90/00* | (2016.01) | |

(52) U.S. Cl.
CPC ............... *A61B 8/485* (2013.01); *A61N 7/02* (2013.01); *A61N 7/022* (2013.01); *A61B 2017/00084* (2013.01); *A61B 2017/00106* (2013.01); *A61B 2090/378* (2016.02); *A61N 2007/0078* (2013.01); *A61N 2007/025* (2013.01)

(56) References Cited

U.S. PATENT DOCUMENTS

| | | |
|---|---|---|
| 6,050,943 A | 4/2000 | Slayton et al. |
| 6,413,254 B1 | 7/2002 | Hissong et al. |
| 6,540,679 B2 | 4/2003 | Slayton et al. |
| 8,016,757 B2 | 9/2011 | Kaczkowski et al. |
| 2007/0073151 A1 | 3/2007 | Lee |
| 2008/0039746 A1 | 2/2008 | Hissong et al. |
| 2009/0105588 A1 | 4/2009 | Emelianov et al. |

OTHER PUBLICATIONS

Final Office Action in U.S. Appl. No. 12/712,019 Dated Jul. 18, 2012, 11 pages.
Non-Final Office Action on U.S. Appl. No. 12/712,019 Dated Jan. 28, 2013, 10 pages.
Final Office Action on U.S. Appl. No. 12/712,019 Dated Oct. 25, 2013, 10 pages.
Non-Final Office Action on U.S. Appl. No. 12/712,019 Dated May 14, 2014, 9 pages.
Notice of Allowance on U.S. Appl. No. 12/712,019 Dated Feb. 18, 2015, 8 pages.

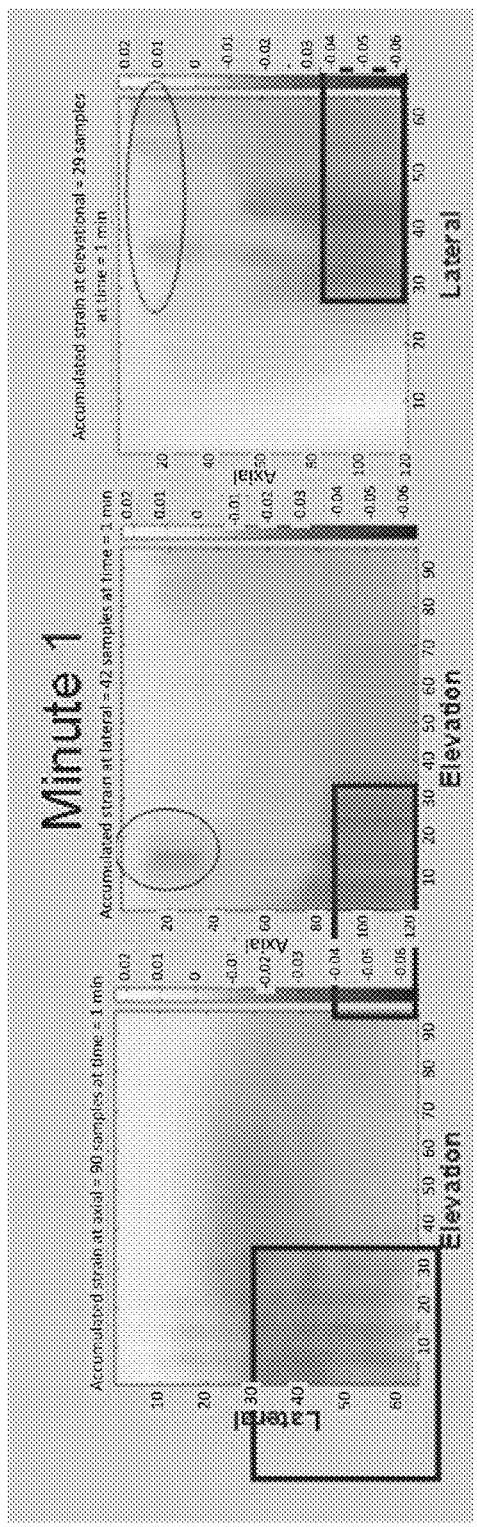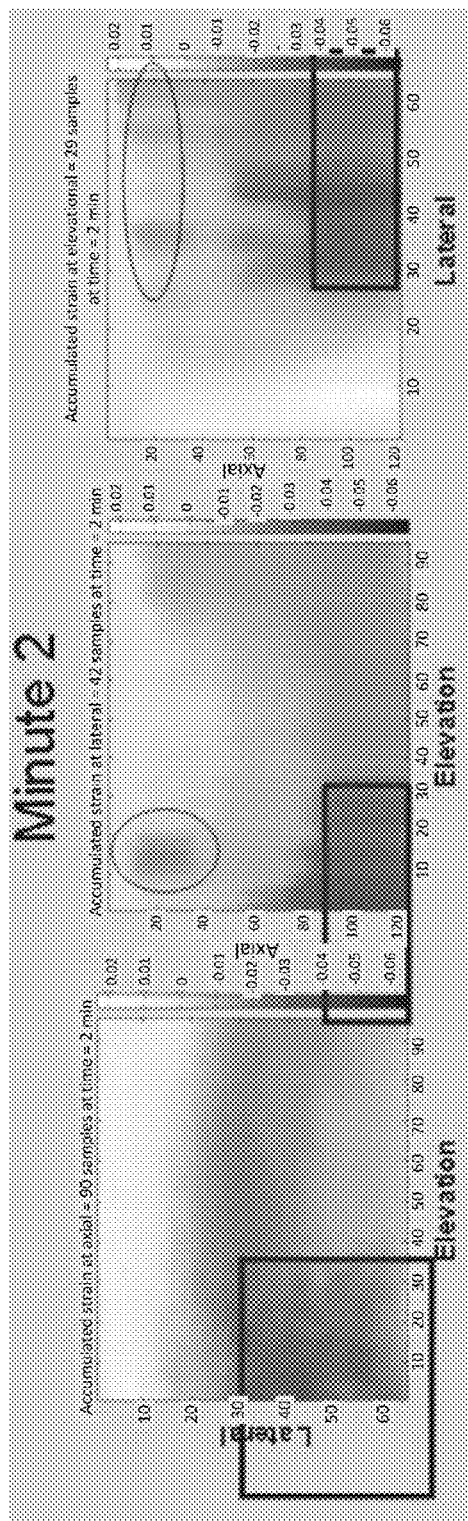
Figure 7C
Figure 7D

REAL TIME THREE-DIMENSIONAL HEAT-INDUCED ECHO-STRAIN IMAGING FOR MONITORING HIGH-INTENSITY ACOUSTIC ABLATION PRODUCED BY CONFORMAL INTERSTITIAL AND EXTERNAL DIRECTIONAL ULTRASOUND THERAPY APPLICATORS

CROSS-REFERENCE TO RELATED PATENT APPLICATIONS

This application is a Continuation of U.S. application Ser. No. 12/712,019, filed Feb. 24, 2010, incorporated herein by reference in its entirety, which claims priority from U.S. Provisional Application 61/155,080, filed Feb. 24, 2009, incorporated herein by reference in its entirety.

BACKGROUND OF THE INVENTION

Many recent studies have demonstrated the efficacy of interstitial ablative approaches for the treatment of malignant and benign tumors, including chemical ablation, cryoablation, and thermal ablation using energy sources like radiofrequency, laser, microwave, or focused ultrasound. Despite these promising results, current systems remain highly dependent on operator skill, and cannot treat many tumors because there is insufficient control of the size and shape of the zone of necrosis, and no control over ablator trajectory or energy directivity within tissue. Remedying this problem requires advances in end-effector design, precise conformability of the ablation volume and shape created by the ablator device to the desired target location, and real-time monitoring of the zone of necrosis to ensure complete treatment. While intra-operative ultrasound imaging has been shown to be a practical and affordable in targeting, simultaneous manual handling of the B-mode ultrasound (US) probe and the ablator device is a challenging task that is prone to significant errors in the hands of even the most experienced physicians. Further, B-mode US imaging is not suitable for accurate real time monitoring of the ablation region to enable feedback control of the size and shape of the lesion. Tissue deformation and target motion make it extremely difficult to place the ablator device into the target. Irregularly shaped target volumes typically require multiple insertions and several overlapping thermal lesions, which are even more challenging to accomplish in a precise and timely manner without causing excessive damage to surrounding normal tissues. In answer to these problems, embodiments described herein provide an innovative method for combined thermal monitoring and accurate tracking and registration with respect to spatially-registered intaoperative US volume. A system incorporating this three-dimensional ultrasound (3DUS) with a high intensity ultrasound ablation tool, Ultrasound Interstitial Thermal Therapy (USITT), capable of actively shaping ablation, under real-time monitoring from registered thermal imaging. Our interstitial and intracavitary high-power ultrasound applicators have demonstrated controllable and penetrating dynamically shaped heating patterns (dynamic adjustment in length, angle, radial penetration), providing an ideal mechanism for precision conformable thermal surgery. This controllability and penetration has the potential to provide a significant improvement over existing radiofrequency (RF) and microwave (MW) technology used for minimally invasive thermal ablation of liver tumors, which are limited to fixed (generally spherical) or unpredictable ablation profiles and comparatively low therapy penetration depth. To date, extensive evaluation of this minimally invasive technology has been limited mostly to in vivo canine prostates and other moderately perfused tissues. In contrast, embodiments of the present invention include a true closed-loop system for placement, guidance, and percutaneous delivery of conformal ultrasound ablative therapy, with on-line monitoring of treatment using thermal imaging.

Current monitoring approaches often result in either positive margins or excessively large ablation zones in order to achieve negative margins. Some ablative devices employ integrated thermistors or thermocouples for temperature monitoring. However, these temperature readings only provide a crude estimate of the true zone of ablation. Non-invasive monitoring options include US, magnetic resonance, CT, and X-ray fluoroscopy.

Ultrasound Imaging. Conventional ultrasonographic appearance of ablated tumors only reveals hyperechoic areas due to microbubbles and outgasing. According to Kolen et al. [Kolen-2003], high-intensity focused ultrasound ("HIFU") experiments show that B-mode imaging is generally inadequate. The size and shape of the hyperechoic region in the B-mode does not necessarily correspond to the damage seen on the gross-pathology pictures.

MRI Imaging. Magnetic resonance imaging can monitor temperature changes (MR thermometry), but is expensive, limited in availability, difficult to use intraoperatively, not real time, and lacks implementation flexibility. MR thermometry provides low frame rates and requires specific MRI-compatible equipment. [Graham-1999].

CT and X-ray. These technologies are capable of measuring soft tissue mass density changes. Salas et al. [Salas-2004] introduced a new method that should aid all thermal ablative techniques. The method requires an X-ray imaging system with a digital detector. During ablation, periodic X-ray exposures are taken and subtracted from a baseline pre-ablation regional X-ray mask. Successive subtracted images show the propagation of the change in density, which is indicative of coagulation.

Ultrasound Elasticity Imaging (USEI). This imaging modality has emerged as a useful augmentation to conventional US imaging. USEI has been made possible by two discoveries: (1) different tissues may have significant differences in mechanical properties and (2) the information encoded in the coherent scattering (a.k.a. speckles) is sufficient to calculate these differences following a mechanical stimulus [Ophir-1991]. An array of parameters, such as velocity of vibration, displacement, strain, strain rate, velocity of wave propagation and elastic modulus, have been successfully estimated [Konofagou-2004, Greenleaf-2003], which makes it possible to differentiate stiffer tissue masses, such as tumors [Hall-2002, Lyshchik-2005], or ablated lesions [Varghese-2004].

Ultrasound Thermal Imaging. Temperature estimation algorithms using ultrasound are very similar to strain estimation; both attempt to solve similar time-delay estimation problems. FIG. 1 represents the main concept of heat-induced echo-strain. Prior to target zone heating: the overlay represents the same speed of sound (i.e. same temperature). During ablation: the overlay represents the hot area in the middle with higher speed of sound. By tracking shifts in the backscattered RF signals, heat-induced strain can be generated, as shown in the strain profile, where low strain corresponds to constant temperature and high strain to higher temperature. The induced shift in the RF backscattered signals is related to both changes in speed of sound and thermal expansion, which can be calibrated to correspond to temperature. Two-dimensional temperature estimation using pulse-echo diagnostic ultrasound has been previously described by Ebbini et al. [Seip-1995, Simon-1997], by Damianou et al. [Maass-1996] and by Varghese et al. [Varghese-2002]. Measurement models in both time and frequency domains have been proposed in the literature [Amini-2005, Anand-2007, Maleke-2008].

SUMMARY OF THE INVENTION

One advantage of using an ultrasound-based monitoring approach including elasticity and thermal imaging is that it can be utilized and applied intraoperatively during the intervention without moving the patient to the MRI or CT scanner room or disrupting current clinical workflow. A second advantage is use of thermal imaging feedback to control the size, shape and intensity of a multi-transducer high power ablator tool.

In one embodiment, the present invention includes a three-dimensional thermal imaging system using a mechanical three-dimensional ultrasound (3D US) probe to monitor interstitially and externally applied ultrasound ablation. It is believed that three-dimensional thermal imaging can overcome the limitations and problems associated with the 2D approaches wherein motion compensation and a larger field of view are required. In particular, 3D is extremely useful for detecting out-of-plane motion. However, with this transition to 3D, several new challenges arise: primarily, the computational cost, then the motion compensation problem, and third the competence of current 3D ultrasound probe technology. Finally, visualization in the most useful form becomes a concern as well. Embodiments of the present invention address these problems. In one embodiment, the present invention comprises computer readable medium containing a parallelized algorithm that can run on a GPU and can generate rapid temperature maps and delivered thermal dose maps from RF volumes of data that are collected using available 3D mechanical probes. In yet another embodiment, the thermal dose map is electronically coupled to the control of the multi-transducer ablator to control and alter delivered US power to the tissue spatially as well as temporally.

Intra-Procedural Feedback Control:

When a procedure begins with the ultrasound therapy applicator, treatment progress is monitored and delivered treatment is compared to planned thermal dose. As treatment progresses, in one embodiment, the system automatically adjusts power levels of various applicator transducer elements to modify thermal dose in real-time, compensating for unmodeled effects (e.g. varying tissue thermal resistance, blood vessel heat sinks, etc.) In one embodiment, it is possible to simultaneously control intensity to transducer elements differentially to compensate for varying absorption in specific sub-regions of the treatment volume. This process will be dynamically adaptable by the surgeon, who will observe and specify changes to thermal dose plan as therapy delivery progresses. Intra-procedural optimization is made possible through integration of the non-invasive treatment monitoring and 3D registration, correlation with the treatment plan, and closed-loop control based on thermal monitoring measurements.

BRIEF DESCRIPTION OF THE DRAWINGS

FIG. 3A Interstititial USITT applicator, FIG. 3B External/Shallow focus HIFU applicator.
FIG. 7A-7F. Ex-vivo chicken HIFU ablation experiment.
FIG. 7A The chicken sample after ablation (gross-pathology pictures) with the thermal lesion.
FIG. 7B 3D B-mode US sections.
FIG. 7C-FIG. 7F 3D thermal strain sections every minute of ablation from the first to the fourth minute, respectively.

DETAILED DESCRIPTION OF THE PREFERRED EMBODIMENTS

One embodiment of the present invention relates to a new system with integrated ultrasound ablator which is spatially-registered with 3D ultrasound image guidance and real-time treatment monitoring based upon echo-strain and temperature estimation performed in real time using GPU parallelization.

System Setup

Figure 1:
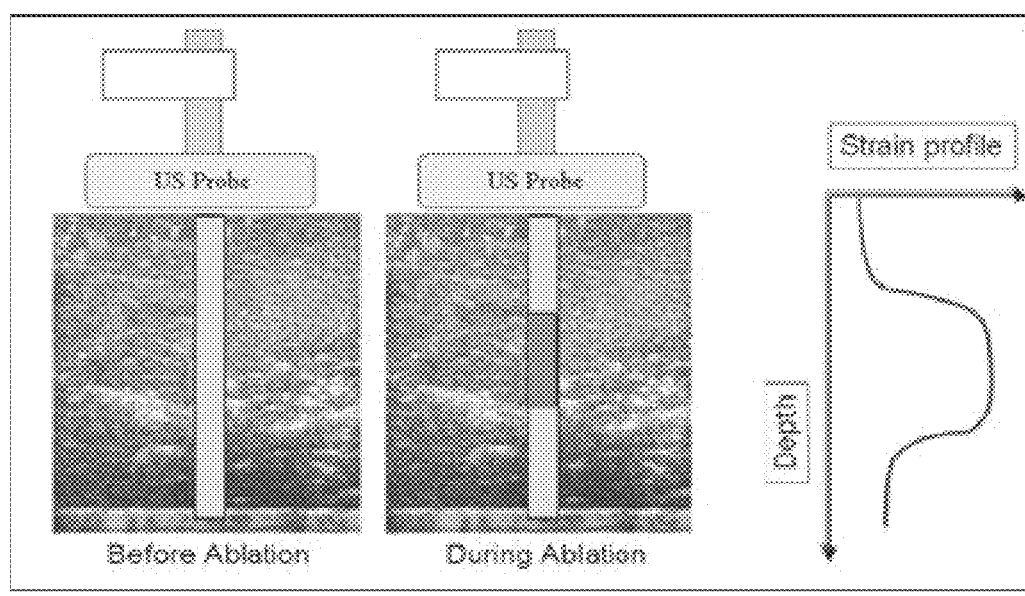
FIG. 1. Heat-induced echo-strain concept.
Figure 2:
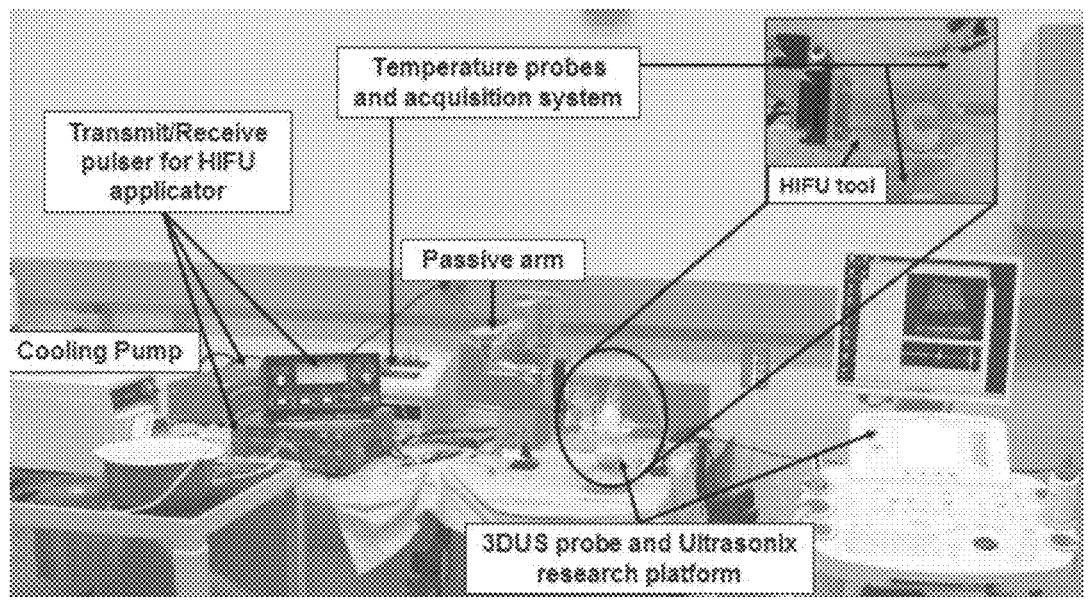
FIG. 2. Setup for a 3D ultrasound thermal monitoring for HIFU ablation.

FIG. 2 illustrates one embodiment of a system 101 of the present invention. The main components are: a multi-channel HIFU pulser/receiver unit 103, a data-logger 105 for data acquisition from two thermocouples 107a, 107b, a passive peristaltic pump with fluid circulation 109 for cooling the HIFU applicators 103, and the ultrasound system 111.

Ultrasound Setup: Ultrasound data acquisition as described here was conducted using a Sonix RP diagnostic ultrasound system -from Ultrasonix, Inc. (Richmond, BC, Canada)—packaged with an open research interface. One of ordinary skill would appreciate that various known acquisition mechanisms, including other commercially available software suites, would be adaptable to the system as described herein. In one embodiment, the data acquisition interface enables 3D RF data acquisition with optional automatic or manual control of the motor on the 4D probes. In the embodiment illustrated in FIG. 2, the 3D C3-6/40EP probe had an Azimuth radius of 38.41 mm, 128 elements, 4.5 MHz central frequency with fractional bandwidth 50%, and a stepper motor of 0.062°/step. The ultrasound probe is attached to a 6-DOF passive arm with a break that locks the whole arm at any location in space as shown in FIG. 2. While this implementation used a Sonix RP imaging system, in principle any ultrasound imaging system providing access to RF data and control of probe stepping could be used.

Acquisition Software: For purposes of the examples described herein, the acquisition software used to obtain the data was "Porta", a C++ software development kit (SDK) for the Sonix RP ultrasound scanner. The acquisition software is named Propello that is built using the Porta SDK. Propello takes advantage of the ultrasound scanner's research capabilities, namely the ability to have full control over the stepper motors of specific transducers, and the ability to collect the beam-formed radio-frequency (RF) data. By combining these two features, Propello offers a unique way to acquire volumetric RF data that cannot currently be performed on other similar research ultrasound devices. In one embodiment, the acquisition system has two acquisition modes: manual mode, where the user supplies commands to step the motor, and an automatic mode, where the motor sweeps continuously based on parameters supplied by the user. While the motor is driving the transducer scanhead, both the RF and grayscale data can be acquired individually or collectively. The advantage of collectively acquiring the data together is to obtain a reference B-mode image for each RF frame, thereby reducing the post-collection processing needed to further transform the RF data collected.

Figure 3A:
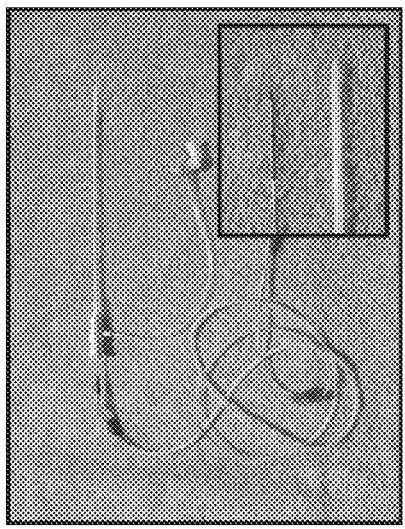
FIGS. 3A and 3B. HIFU applicators.
Figure 3A:
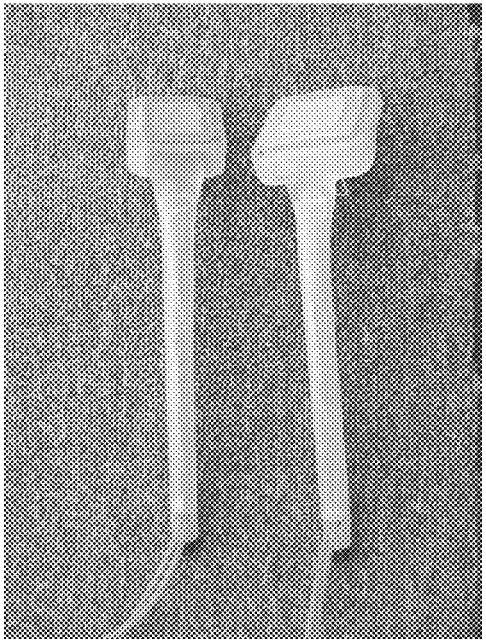
Figure 3A:
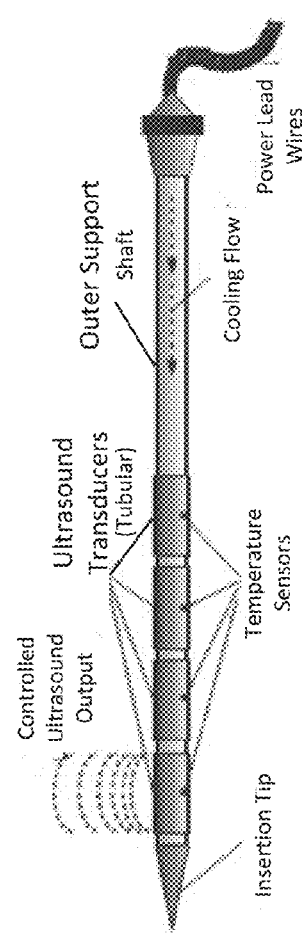
Figure 3B:
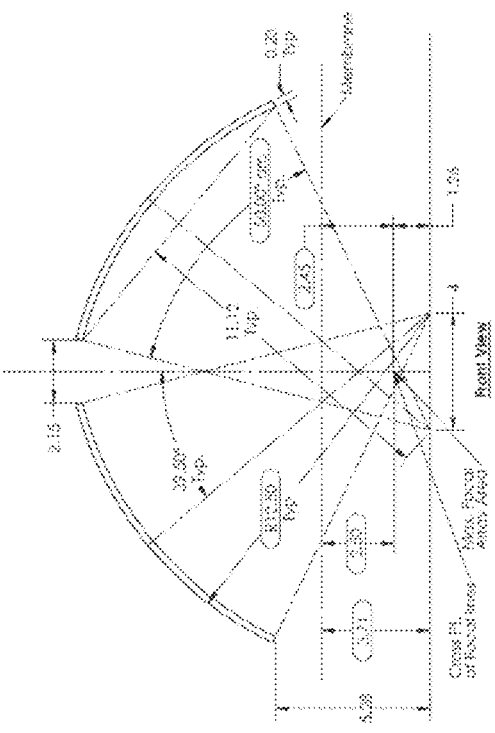

HIFU Setup: The HIFU system employs ablation using either interstitial ablators USITT or external applicators as shown in FIG. 3. The interstitial catheters and needles (FIG. 3A) permit direct insertion into the tissue or insertion through a natural cavity or vessel and control several treatment-specific parameters such as angle width and position, depth profile, and radial power deposition. This permits creation of a truly conformable treatment pattern. In one embodiment, the device used is capable of depositing sufficient power to produce an ablative zone of 5 cc to 50 cc in an insonation period of 1-5 minutes. This needle/catheter based applicator can consist of multiple directional or omni-directional transducers operating at the same or different frequencies can be driven over a wide range of power levels. In these experiments, the USITT is driven at a frequency of 8.3 MHz by a 20-W driving power and operates in a 180° insonification angle around the central axis of the applicator. The acoustic power delivered to the tissue, however, is approximately 8 watts (due to overall RF-to-acoustic conversion efficiency and including power reflection of about 4%). The other type of ablator used in our experiments was an external applicator that deposits a focused thermal dose via surface contact with tissue. It is connected to the HIFU system to create tissue ablation that extends only a few millimeters ~3-10 mm beneath the point of contact of the ablator and tissue surface creating a rectangular or ellipsoidal ablative zone along the elevation of two piezoelectric elements that are excited by 11 MHz continuous wave at 20-30 W per channel, creating volume focal zones much larger than typical HIFU devices. We have designed and tested other applicators which are designed to focus at depths varying from 3 mm to 50 mm with lateral zones at the focal depth from 2 $mm^2$ to 120 $mm^2$. In the examples described herein, data was collected from a set of tissue phantoms containing chicken breast extending in the elevation and lateral dimensions of the tissue ablator (FIG. 3B).

EXAMPLES

Preliminary ex-vivo experiments were conducted in four specimen of chicken muscle, which had been immersed in warm water to help degas the tissue and maximize the transmitted power of the acoustic ablator. Samples used were approximately 7×7 cm in size; these were cut from the degassed tissue and embedded in gel phantoms to provide mechanical support to the sample and to the thermocouples.

Figure 4:
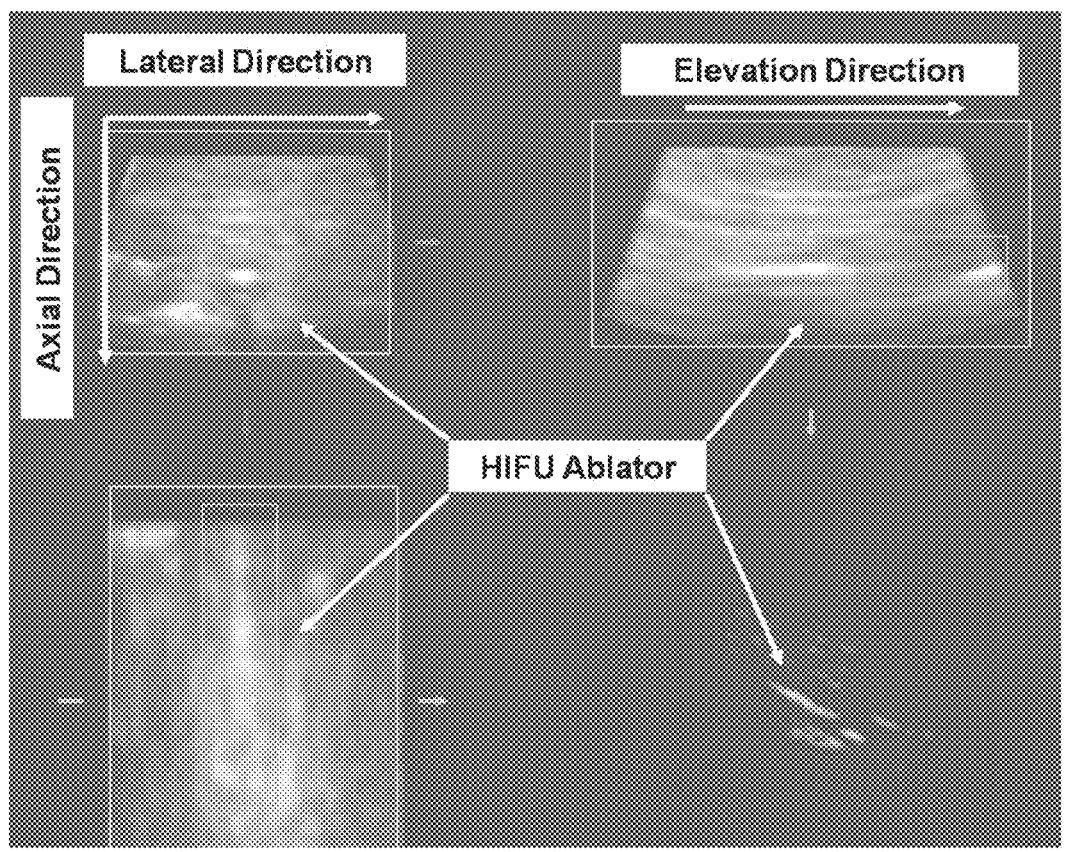
FIG. 4. 3D US reconstruction and volume rendering with the HIFU ablator.
Figure 7A:
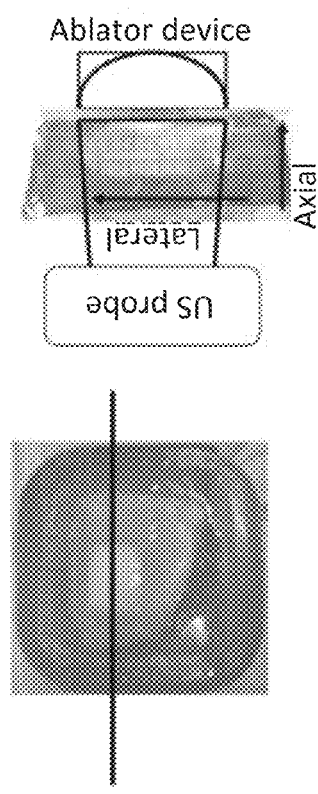
Figure 7B:
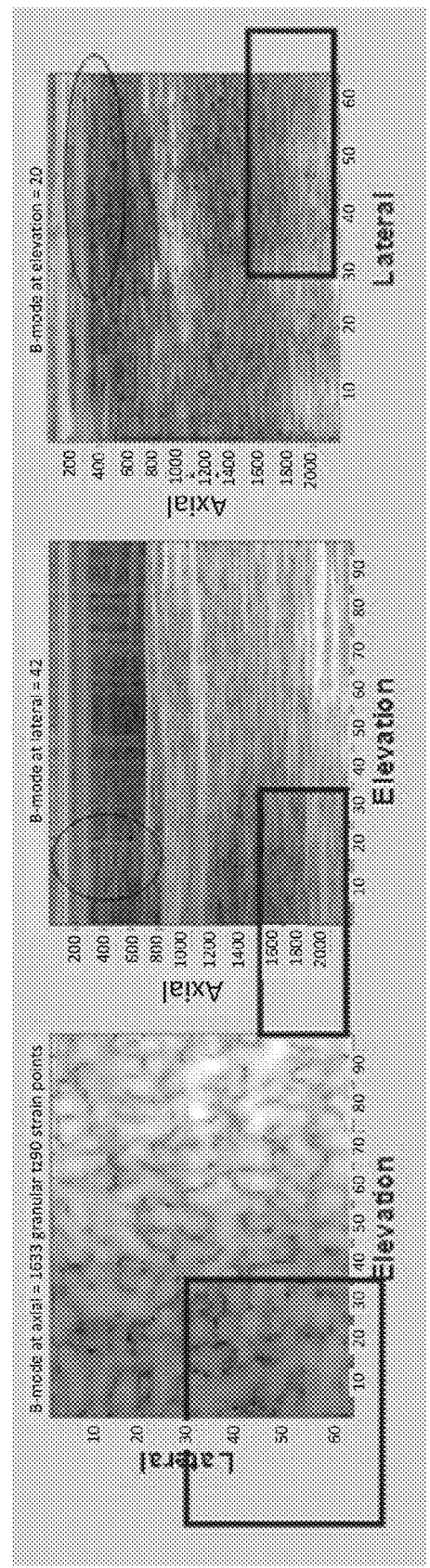
Figure 7E:
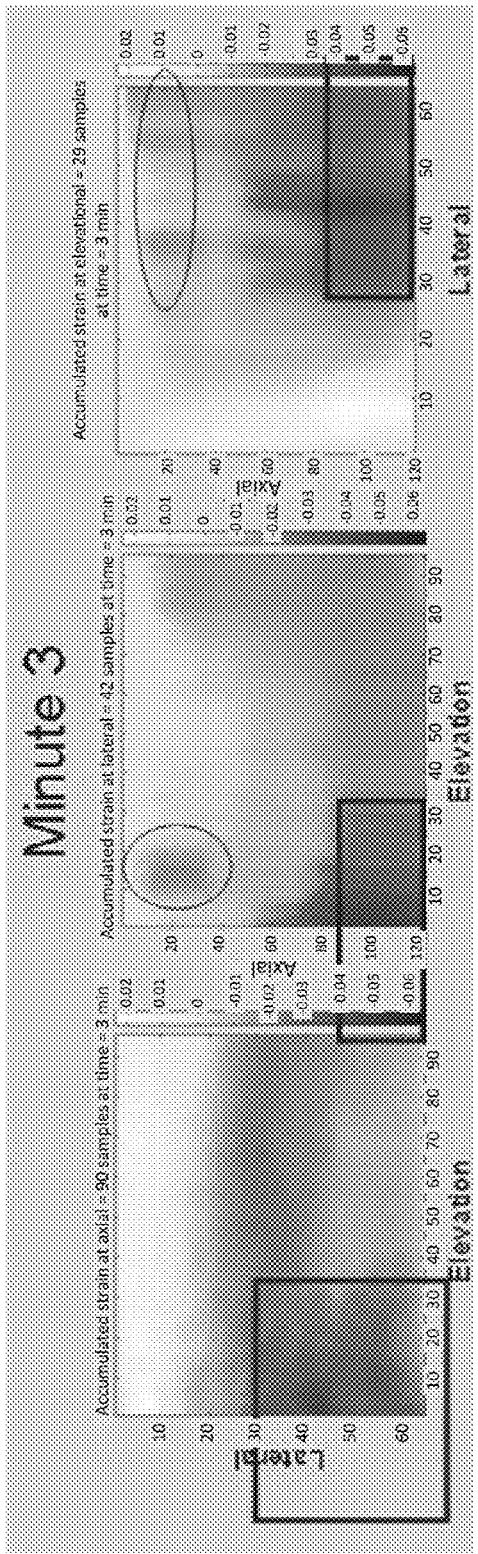
Figure 7F:
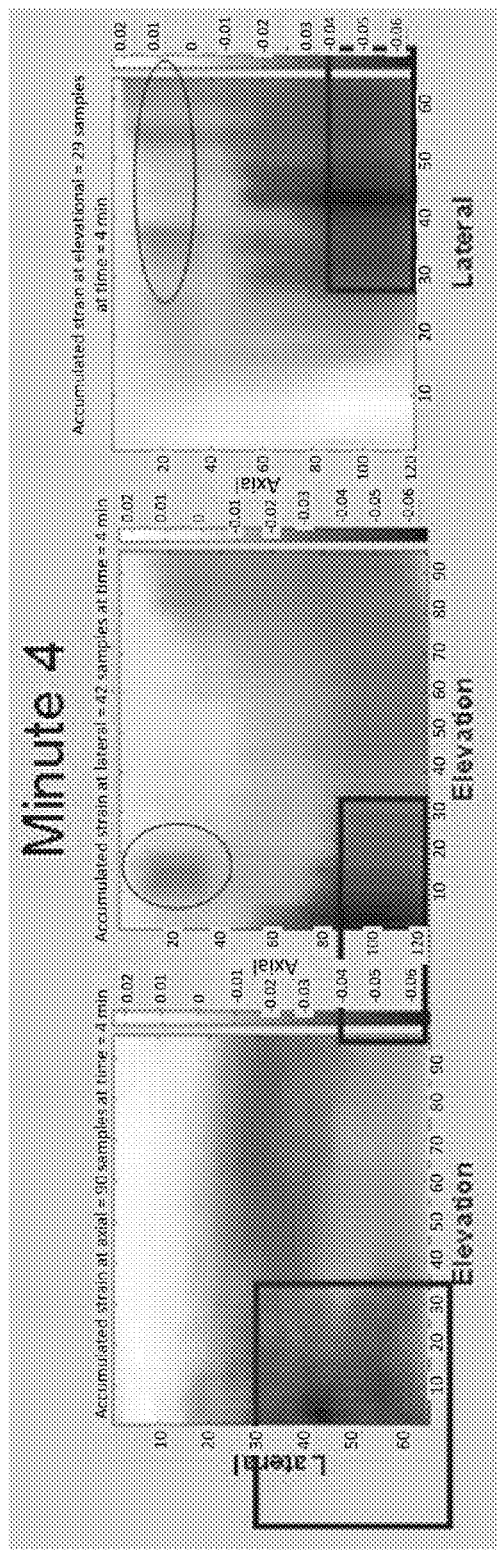

Using the interstitial needle applicator, the HIFU ablator was inserted so that the 180° insonification semi-cylinder is directed to face the 3D US probe placed on top of the sample as show in FIG. 4. The 3D US volume was collected by rotating the 1D array about an axis perpendicular to the inserted HIFU ablator shaft; hence, at any given image of this volume, the applicator will be seen as one point. Both thermocouples had been placed in the axial-lateral plane at the 90° elevation plane inside the tissue sample and are thus perpendicular to the HIFU shaft as shown in FIG. 4. Similarly, the HIFU external applicator (FIG. 3B) was placed on one side of the phantom facing directly the chicken muscle, where the 3D US probe was placed on the other side as shown in FIG. 7A. The 3D US volume was collected so that at certain images of this volume, the two applicators forming a semicircle cross-section will be seen underneath the chicken muscle.

Figure 5:
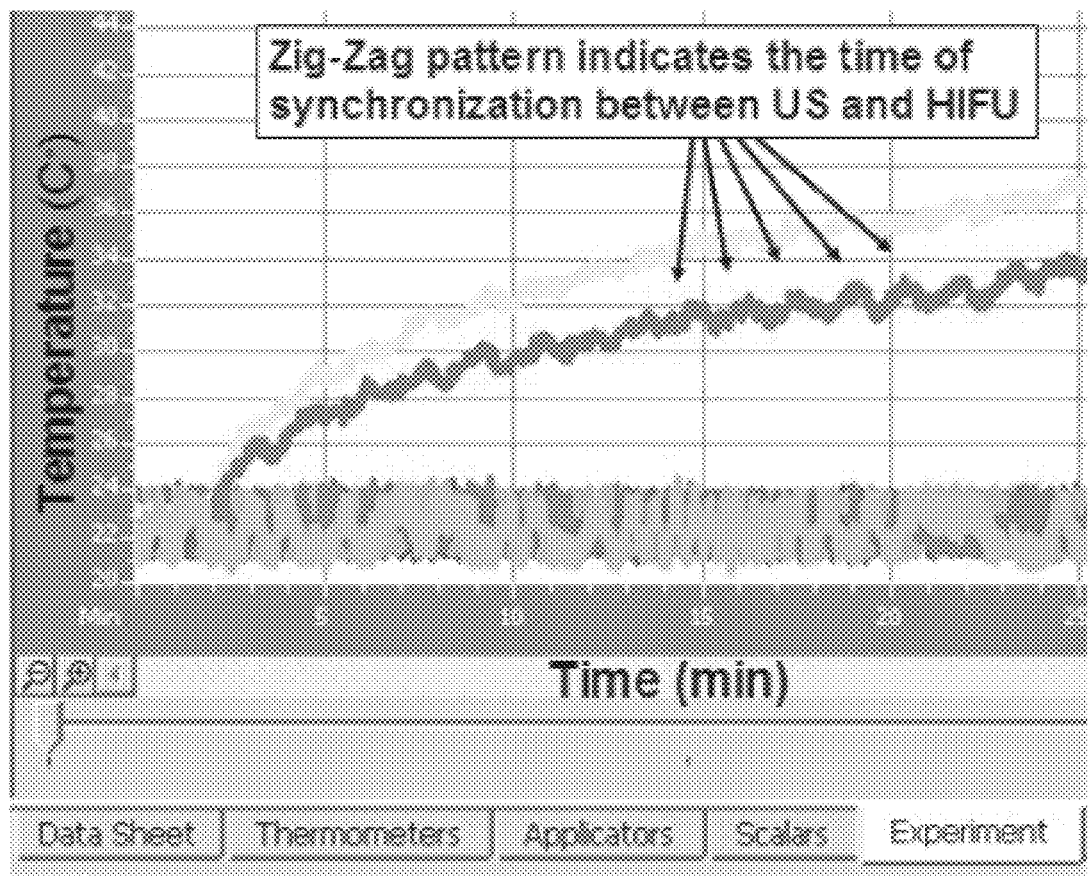
FIG. 5. Thermal recording.

The imaging transducer wobbler motor step was set to 0.065° in one experiment with an approximate 7.75° FOV and 0.25° in another experiment with a corresponding 31.25° FOV. The experiment started by collecting a base 3D RF ultrasound volume with simultaneous temperature acquisition using both probes. The emission of HIFU energy was periodically interrupted to avoid interference between the two ultrasound beams (tracking/imaging and therapeutic). The interruption period was 2-4 seconds, whereas, the HIFU period was equal to 60 seconds, resulting in a HIFU duty cycle that is above 90%. Experiments were conducted for 5-20 minutes of insonation and the thermal recording as reported by the thermocouples is shown in FIG. 5.

Algorithm

The use of a heat-induced strain algorithm was deployed and parallelized in the above described examples. The main processing steps are briefly described hereunder:
1. Instantaneous displacements are estimated from time delays between consecutive 3D RF volumes (volumes are collected every minute) using normalized cross-correlation. A correlation window of 8-16 $\lambda$ is used, where $\lambda$ is the wavelength of the acoustic signal (16 $\lambda$ is equivalent to 5.33 mm in the case of central frequency equal to 4.5 MHz and sampling frequency equal to 20 MHz). The overlap is chosen to be 85% of the correlation window.
2. Sub-sample interpolation is performed using the cosine fit method.
3. The echo-strain is then obtained by computing the displacement gradient in the axial direction, after smoothing the displacement map through applying a median filter followed by a low pass filter. For strain estimation the gradient is then computed using least squares method with a kernel equal to 8 samples.
4. The previous steps are repeated for all volumes.
5. Then, strain volumes are accumulated for every minute of insonation. The accumulation process is accompanied with shift correction taken into consideration, in order to compensate for motion artifacts that arise in three dimensional ultrasound imaging due to either motion induced by the slippage of the tissue sample, or the positional error of the 3D US wobbler motor.

Parallel Implementation

As described above, in one embodiment, the algorithm follows a sequence of steps that are identically repeated for each pair of frames in two consecutive 3D volumes acquired. Moreover, within each frame, several parts of the algorithm are performed on different windows of the 2D pixels in the image and repeated in the exact fashion for other windows of the image, which motivated the benefits of a parallelized implementation of the algorithm to speed up the processing time to enable real time thermal imaging for ablative therapy monitoring.

Multi-core general-purpose GPU cards are now generally available for graphics processing. In one embodiment, parallelization may be applied to the calculation of the echo-strain images using the multi-core Nvidia general-purpose GPU card. These graphics processing units contain many cores, typically ranging from 128 to 240 or more. Each core can be dedicated to perform various functions on different sets of data. Nvidia has provided a parallel computing architecture named CUDA (Compute Unified Device Architecture), which is used for programming and configuring these GPU's. It defines a thread block, which as its name suggests, is a group of threads. A piece of function called kernel can be configured to run on a particular number of blocks and each thread in those blocks performs the same function as specified in the kernel on the same or different dataset. In case of multi-threaded programming, it is important that the function (or, as may be the case, the kernel) be thread safe, ensuring that they do not update global data or shared data without synchronization.

For example, such can be applied to a pair of RF date imagies. In a serial implementation of the algorithm, nested loops are employed. In our case, the value of the pixel in the output image is independent of other neighboring pixels; hence, the deployment of multiple threads, each handling the computation pertaining to individual pixels is intuitive. In this scenario, threads do not need to wait for each other to complete their operations, since they access different memory locations for data transfer and update. Hence, this guarantees that the functions are thread-safe. CUDA allows us to use the loop parallelization technique, wherein functions which had previously invoked the use of loops are converted into a kernel in the parallel implementation. This kernel accepts two parameters, namely the number of blocks and the number of threads per block. This is achieved through the internal assignment of unique identifiers threadIdx and blockIdx to each kernel. These identifiers are structures of three fields each, which denote the three dimensions of threads and blocks respectively. A group of threads is referred to as a block, as previously mentioned. Analogously, a group of blocks is referred to as a grid. Thus, a grid of maximum dimension (grid_x, grid_y, grid_z) can accommodate a number of blocks that is fewer than or equal to grid_x*grid_y*grid_z. For our GPU card, grid_x=grid_y=grid_z=35535 and a block can have a maximum dimension (block_x, block_y, block_z), where block_x+block_y+block_z<=512, i.e. a block can have a maximum of 512 threads. It is to be noted that the number of threads a block can have depends on the number of registers contained inside a kernel. If too many registers are used, then the number of threads per block will decrease. Each of these factors is taken into account during the design of our algorithm.

The initial step of the algorithm is to calculate the number of pixels per RF line (where displacement/strain will be estimated) based on the choice of the correlation window size and the amount of overlap. This number is denoted asm and the number of RF lines as n. An output matrix of size (m×n) is then initialized in the GPU memory, which is commonly referred to as the device memory. The two raw images of RF data are similarly initialized and passed onto the device for memory allocation purposes. A pseudocode module which performs both normalized cross correlation and cosine fit interpolation for each output pixel is defined. Usually, this module written in C is typically implemented using two nested "for" loops, which operate on both the columns and rows of the two input RF data matrices. In one example, this function was adapted for parallel implementation and configured a kernel that is capable of running n blocks with m threads each, which obviates the need for these nested loops. Thus, a total number of (m×n) threads is spawned to execute the kernel in parallel and the loop indices are handled internally. Depending on a specific configuration of CUDA kernel grids and blocks, the evaluation of the loop index variable may change.

Figure 6:
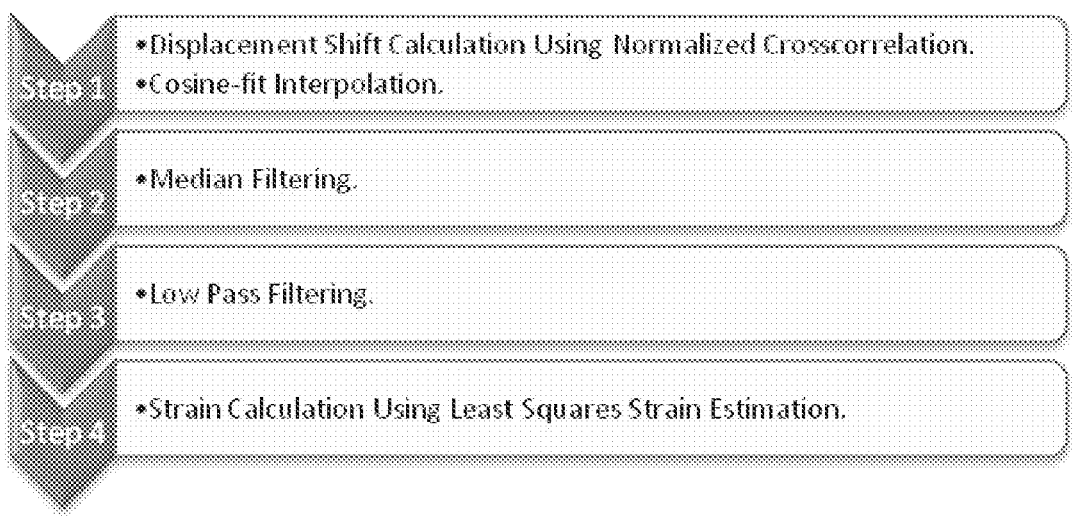
FIG. 6. Steps of the GPU-based temperature estimation algorithm.

For processing p images simultaneously, the images are conceptually aligned adjacent to each other such that image i+1 is to the right side of image i. This simple arrangement made it possible to process all the frames in the two consecutive acquired US volumes at the same time. The result is an increase in the number of threads that are spawned simultaneously. In this case, the total number of threads becomes (n×p)×m, and this configuration for the GPU device leads to a higher I/O efficiency. The same is executed serially for the entire pipeline consisting of the four steps shown in FIG. 6, that eventually generate a volume of strain images. Note that steps 1 to 4 are performed serially since each step needs output from the previous one. These steps are explained in more detail in the previous algorithm Section 2.3. To give a typical estimate of the overall number of threads required to execute each of the four steps, let us assume m=140 strain points per RF line, n=64 RF lines per image, and p=125 images per volume. Thus, given this example, each of the above steps needs 1,120,000 threads to update each pair of volumes.

Results and Discussion

Three-Dimensional Imaging Using 3D US Mechanical Probes

Four different experiments were conducted as described above. The first two were using the interstitial applicator (FIG. 3A), and the second two were using the external/shallow-focus applicator (FIG. 3B). For each applicator, as mentioned above, two experiments were conducted with motor step equals 0.25° for the first and 0.062° for the second. The first setting of 125 frames/volume gives coverage of 31.25° FOV, and the second gives 7.75° FOV. Typical thermal recordings with external thermocouples and 3DUS reconstruction are shown and described in Section 2.2. From the experimental observations, there is good agreement with both gross-pathology measurements after terminating the experiment, and with thermocouples readings. The growing thermal strain pattern of the thermal lesion is in accordance with those reported using thermocouple mapping [See, Deardorff-1999, Nau et al-2001].

Results from the first experiment using external/shallow-focus applicator are shown in FIG. 7. For this experiment, the motor step was set to 0.25° with a corresponding 31.25° FOV (i.e. 125 frames per volume). It is to be noted that the reported 3D thermal images/volumes were not scan-converted into mm scale. In the B-mode axial direction, the 2150 RF samples correspond to 40.3 mm; in the lateral direction, 64 samples correspond to 20 mm next to the probe head. Similarly, in the strain image the 124 strain points located axially correspond to 40.3 mm.

FIG. 7A shows the experimental setup and the configuration of both the HIFU ablator and the 3DUS mechanical probe. The image on the left shows a top view of the chicken muscle embedded in a supporting gel phantom. The HIFU external applicator was placed on that side where the white rectangular necrotic area is shown. The size of this ablation is approximately 20 mm by 20 mm and the depth is about 8-9 mm. The overlay black line in the left picture indicates the location where the phantom was cut into two pieces. The right picture shows one half of this phantom placed to show the side view of this chicken phantom. Furthermore, the external HIFU applicator, made from two elements shaping a semi-cylinder transducer, is located on the right side; and the 3DUS mechanical probe is facing the HIFU applicator and is placed on the left side of the phantom.

Both thermal and B-mode images are shown in FIG. 7B-7F. The B-row represents B-mode ultrasound images; The C-row represents thermal images after one minute ablation; the D-row shows the second minute; the E-row is the third minute; and the F-row is the fourth ablation minute. The images in each row are placed in the following order: 1) The left image is a lateral-elevation section (c-scan) taken in the middle of the ablation zone. This section should show rectangular thermal dose similar to the necrosis shown in the left picture in FIG. 7A. Note that the 3DUS volume of interest (VOI) doesn't cover the whole ablation area. The overlay black rectangle shows the location of this ablation zone with respect to the current VOI. Thermal imaging from the VOI was used to control the power to the ultrasound ablator used. 2) The middle image is an axial-elevation section taken at the middle of the ablation zone in the lateral direction. Also, note the black rectangle with respect to the current VOI which was also used in power control to the ablator. 3) The right image is an axial-lateral section taken at the middle of ablation zone in the elevation direction.

The resulting thermal-induced strain images agree with the shape of ablation in the gross-pathology pictures. The ablation appears as a rectangular shape in the lateral-elevation section, while it appears as an elongated ellipse or rectangle with narrow ends at both axial-elevation and axial-lateral sections. However, there are concentrated thermal dose (high strain values) in areas labeled by circles, and ellipses in the axial-elevation, and axial-lateral sections, respectively. These noisy artifact spots can be easily identified and removed as they correspond to areas with small correlation coefficients, located in the surrounding gel materials. The B-mode images clearly show the location of these spots.

Figure 8:
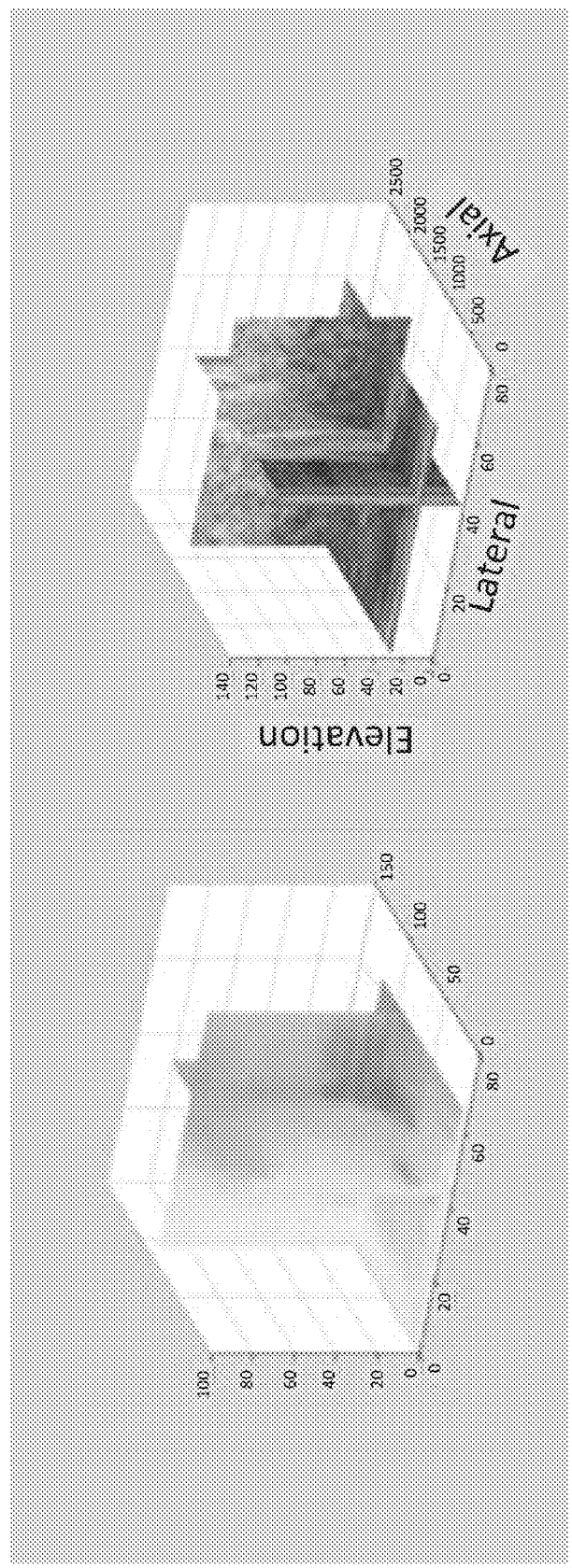
FIG. 8. 3D thermal images after one minute of ablation with corresponding 3D B-mode images.

As mentioned previously, visualization of 3D temperature imaging strain data becomes a challenging task. It should be appreciated that presenting the results as described in FIG. 7 will make it extremely difficult to interpret. In accordance with the present invention, all three cross-sections can be combined as shown in FIG. 8, displaying thermal imaging data and B-scan data. These data may be fused and blended to reveal thermal dose data on the B-scan as well.

Computational Time Study

Figure 9:
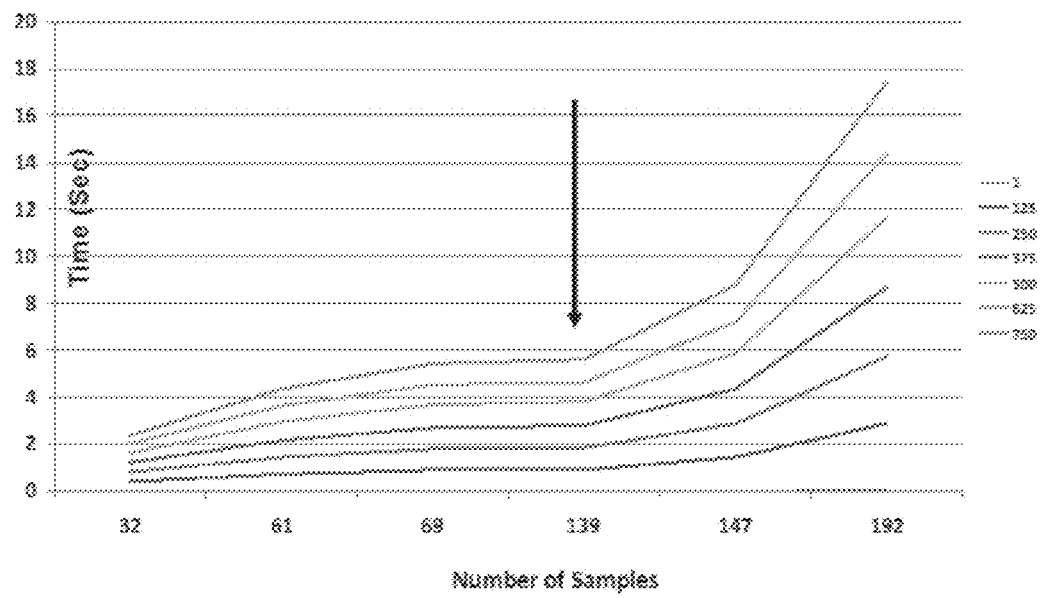
FIG. 9. Computational time vs. number of samples per RF line.

In one embodiment, parallelization may be applied to the calculation of the thermal monitoring images and to the multichannel ablation power control. The parallelized implementation using CUDA has been tested on an NVidia GeForce 9800 GX2 GPU card with 512 MB RAM and with an Intel Quad Core Q9400 CPU host CPU and a 8 GB RAM. Initially, the performance of code in accordance with the principles of the present invention was tested on the GPU card as a function of both the volume size and the number of sample points (strain points per RF line). In one embodiment, the volume size ranges from 1 image to 750 images per volume. Typically, this parameter is in the range of 50-200 images per volume; and in our case using the 3D mechanical probe, it is set to be 125 images per volume. However, testing was performed with up to 750 images per volume (6 times larger than a typical size of 125 images) for the following reasons: 1) to identify the best operation range/point for our algorithm under significant computational load, 2) to evaluate future expansions of our correlation-based algorithm from 1D to 2D/3D. FIG. 9 shows the increase in computational time associated with the increase in the number of sample points. From the figure, one can notice the following: 1) for the number of samples ranges from 32 to 140, the computational time for a typical volume of size 125 frames is less than one second, 2) given the number of samples=32, almost all the volumes (from 1 to 750 frames) run under 2 seconds, 3) a steady performance can be noted in the range from 65-140 samples for all the volumes, and 4) the black arrow in the figure indicates the start of the GPU performance degradation from 140-147, which also intensifies after 147 samples. It is important to mention that all reported results in this section are the average of twenty independent runs with a standard deviation around 1 ms.

Figure 10:
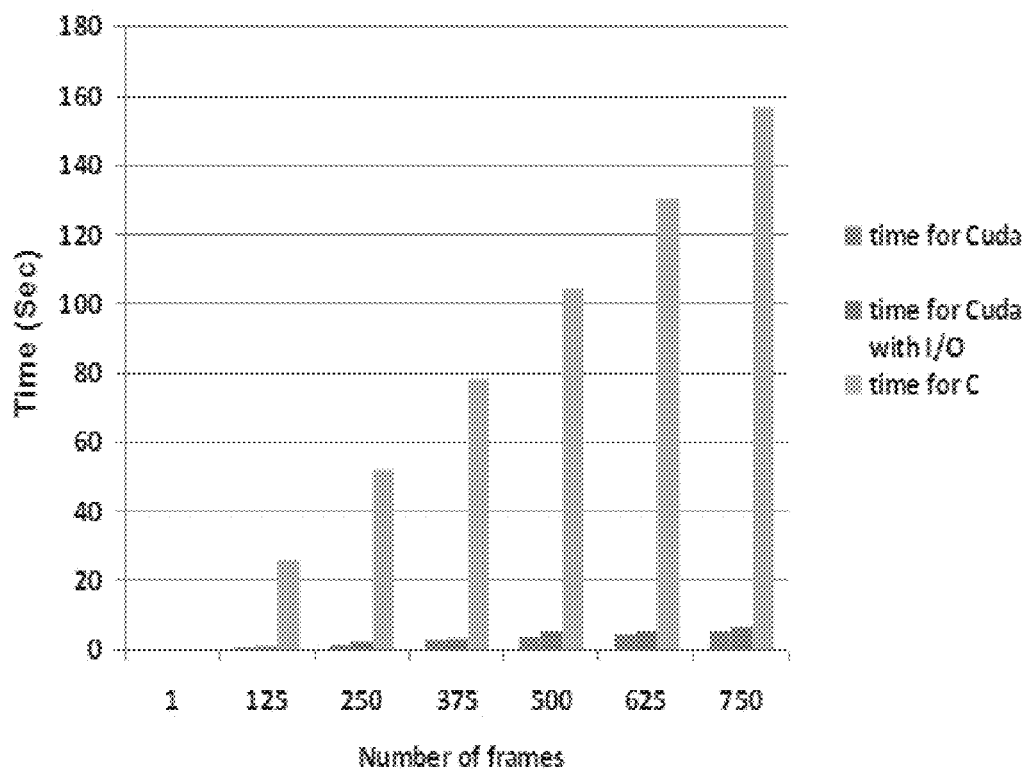
FIG. 10. Computational time for CUDA vs. C code.
Figure 11:
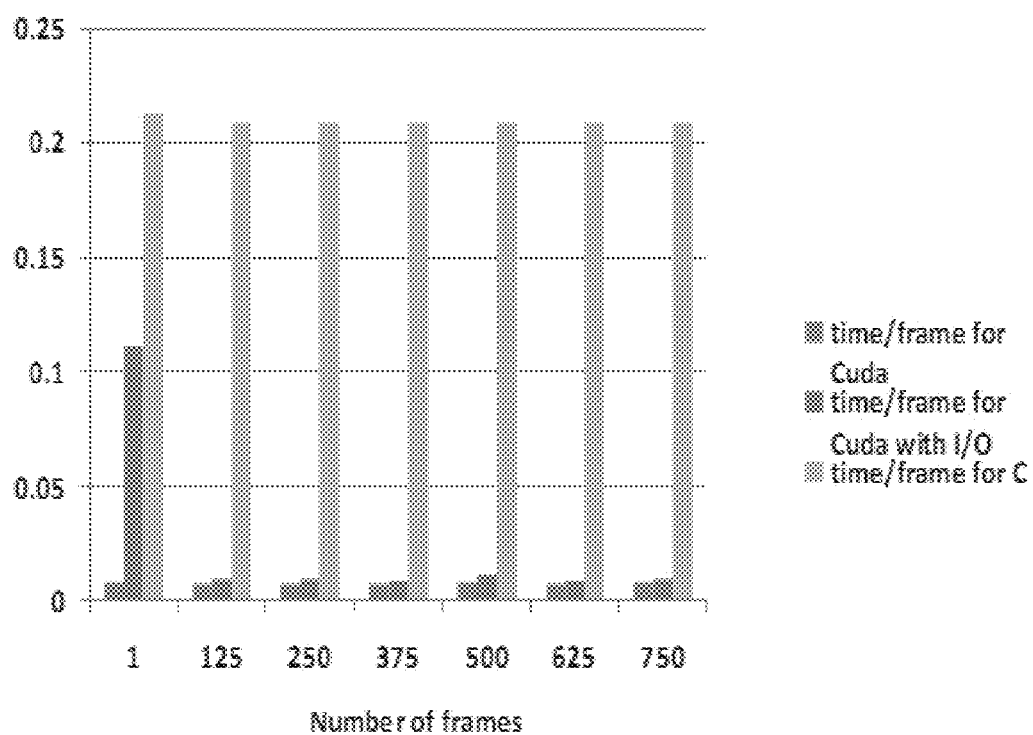
FIG. 11. Normalized computational time per frame for CUDA vs. C code.

Another study has been performed where the number of sampling points was fixed to 139, where optimal utilization was found (FIG. 9). Equivalent C implementation performance is also shown in FIG. 10 and FIG. 11. As expected, it is observed that CUDA implementation is much faster than the C implementation. Specifically, it is about 28 times faster than the C implementation if we do not take into account the time to transfer the data between the host (CPU) memory and the device (GPU) memory. With the I/O taken into consideration, it is still 22 times faster.

It is worth noting that if the number of frame pairs that needs to be processed in parallel increases above a certain bound (determined by the hardware), an implementation that utilizes all three dimensions of the grids and blocks may be required. For instance, for the card used in the described examples, the number of blocks in dimension x has a maximum limit of 65535. Consequently, the number of images that can be processed at a time would be 65535/n, where n is the number of columns per image if images are aligned horizontally.

Motion Compensation

Figure 12:
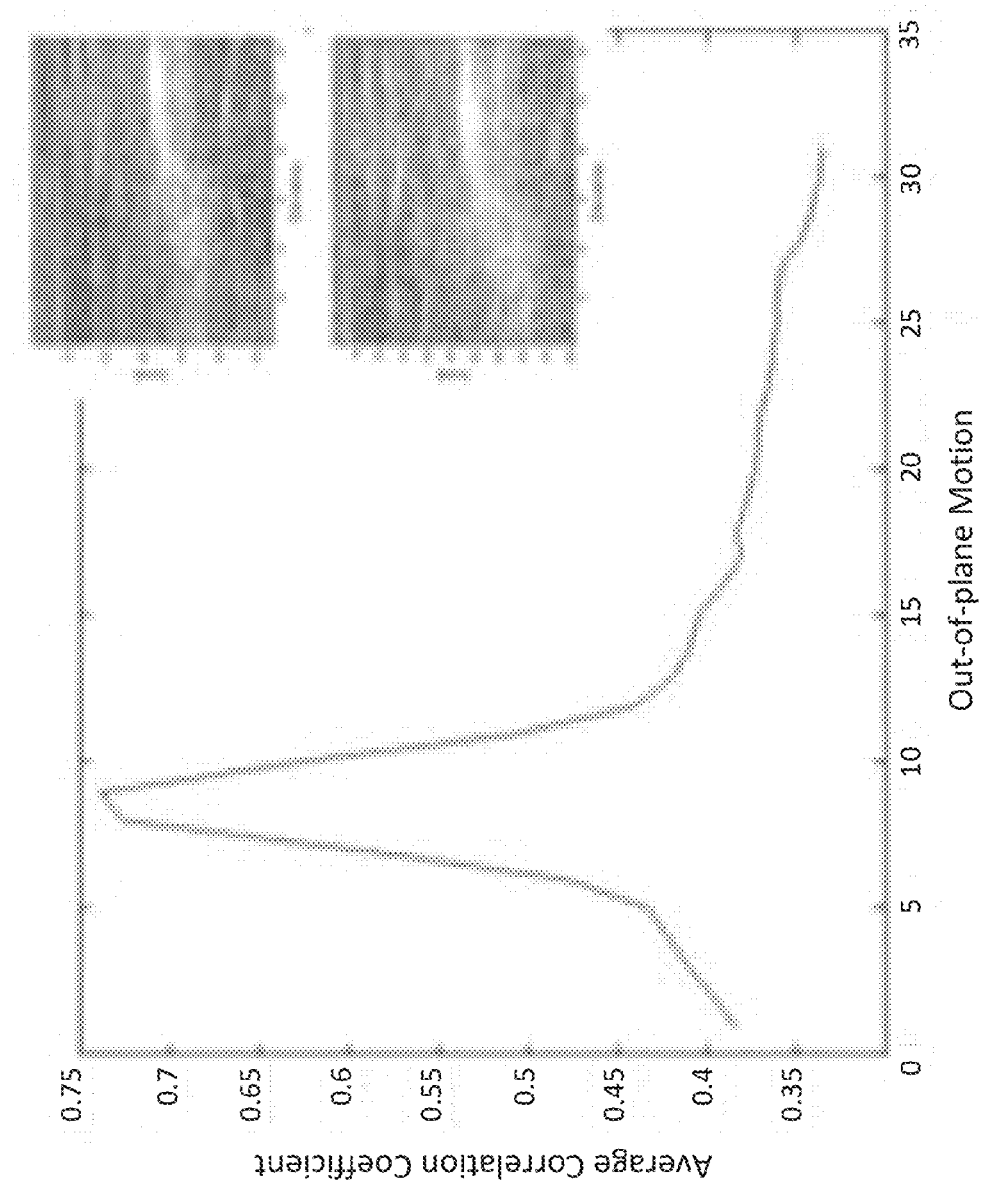
FIG. 12. Motion compensation in the elevation direction due to 3DUS probe motor's position error.

Certain embodiments of the present invention also address the feasibility of motion artifact compensation using three dimensional ultrasound data. For example, in a controlled laboratory environment, there are two types of motion artifacts: 1) motion induced by slippage of the tissue sample, 2) and 3DUS probe motor's position error. FIG. 12 shows an example of recovering this motion rapidly by maximizing the average correlation coefficient in the elevation direction. The motion compensation step has to be done before running the correlation algorithm on this volume-pair.

The embodiments described above generally present an integrated system that consists of high-intensity ultrasound ablators, an ultrasound system, three-dimensional US mechanical probes and a thermal imaging algorithm for monitoring and controlling interstitial and externally-coupled high intensity ablation. Further, certain embodiments utilize a parallelized implementation on GPUs for thermal imaging using the 3D probes. It has been shown that rapid processing of 3DRF data to generate 3D thermal maps within 0.5-5 seconds is achievable using GPU cards. This demonstrates that a real-time implementation of this method is feasible. Good results were also obtained for motion compensation in the 3D US volume, which can account for artifacts that may result from wobblier error or patient motion in a practical setting. The examples above demonstrate that the performance of currently available 3D mechanical probes is acceptable; however, there are several problems that need to be carefully handled. To mention a couple of these, motor stepping errors and lack of encoders in existing ultrasound systems are two limitations that we are addressing with new design revisions. Finally, real-time visualization is another issue with the transition to 3D US technology, and more work on novel volume rendering methods is needed. Thus, it is believed that the above examples also demonstrated the ability to control the ultrasound high intensity therapy applicators using feedback from the real time GPU processed thermal monitoring images.

In summary, current results illustrate the realization of a full 3D thermal imaging system for monitoring high-intensity ultrasound ablation that will potentially outperform other existing methods. Three dimensional imaging has the advantage of combating the known limitations of 2D methods, but it comes with other new challenges. More work is underway in our research group for this system to find its way to clinical practice and eventually improve the therapeutic outcome of ablative procedures in general, and those that are targeted to the treatment of prostate, kidney, and primary and metastatic liver cancer in particular.

What is claimed is:

1. A system for thermal treatment or ablation of tissue comprising:
    an ultrasonic thermal ablation probe including one or more ultrasonic transducers;
    an ultrasonic three-dimensional imaging probe configured to capture at least one image from radio frequency image data obtained before the radio frequency image data is processed;
    a control system for multi-axis control of the imaging probe's position; and
    an ultrasonic feedback mechanism configured to measure ultrasound echo strain to estimate heat-induced structural changes of an area surrounding the ultrasonic thermal ablation probe, from the at least one image,
    wherein the ultrasonic thermal ablation probe comprises one of:
    an interstitial ablator configured to be inserted into tissue, a natural cavity or a vessel to emit high intensity ultrasound energy to deposit thermal dose, or
    an external applicator configured to emit a directional high intensity ultrasound energy to deposit thermal dose via surface contact with tissue,
    wherein control variables of the control system include at least one of a temperature profile or an actual thermal dose profile of a particular location, the temperature profile generated based on the heat-induced structural changes estimated by the ultrasonic feedback mechanism, which control variables are indicative of a level of tissue ablation, and
    wherein the control system receives the estimated heat-induced structural changes from the ultrasonic feedback mechanism and adjusts power levels of the ultrasonic thermal ablation probe based on the estimated heat-induced structural changes.

2. The system of claim 1, wherein the ultrasonic thermal ablation probe is a high-intensity focused ultrasound probe.

3. The system of claim 1, wherein the ultrasonic thermal ablation probe is the interstitial ablator, and the interstitial ablator comprises a needle applicator or a catheter applicator, the needle applicator or catheter applicator having one or more ultrasonic transducers.

4. The system of claim 3, wherein the one or more ultrasonic transducers of the needle applicator or the catheter applicator are semi-cylinder transducers having a 180-degree insonification angle.

5. The system of claim 3, wherein the one or more ultrasonic transducers of the needle applicator or the catheter applicator are multiple directional angles or omni-directional 360-degree transducers.

6. The system of claim 3, wherein the one or more ultrasonic transducers operate at a same frequency or at different frequencies.

7. The system of claim 3, wherein the needle applicator or the catheter applicator has an ablation zone of 5 cc to 50 cc in an insonation period of 1-5 minutes.

8. The system of claim 1, wherein the ultrasonic thermal ablation probe is the external applicator, and the external applicator comprises at least two piezoelectric elements.

9. The system of claim 8, wherein the external applicator creates a rectangular or ellipsoidal ablation zone.

10. The system of claim 8, wherein the external applicator focuses at depths ranging from 3 mm to 50 mm beneath a point of contact of the external applicator and a tissue surface, with lateral zones at a focal depth from 2 $mm^2$ to 120 $mm^2$.

11. A method for real time control of thermal treatment of a tissue region comprising:
    placing an ultrasonic thermal ablation probe in relation to the tissue region to be treated, the ultrasonic thermal ablation probe comprising one of an interstitial ablator or an external applicator;
    placing an ultrasonic three-dimensional imaging probe in relation to the tissue region to be treated and the ultrasonic thermal ablation probe;
    emitting sonic energy from the ultrasonic thermal ablation probe directed at the tissue region;
    monitoring, with the ultrasonic three-dimensional imaging probe, the tissue region, wherein monitoring includes capturing at least one image from radio frequency image data obtained before the radio frequency image data is processed;
    measuring ultrasonic echo strain information regarding the tissue region from the at least one image;
    generating a temperature map for the tissue region based upon changes in the ultrasonic echo strain information for the tissue region, where the changes in the ultrasonic echo strain information are due to increasing thermal dose;
    determining a level of tissue ablation for a particular portion of the tissue region based upon at least one of the temperature map or thermal dose profiles associated with the particular portion of the tissue region; and
    controlling power delivered by the ultrasonic thermal ablation probe based upon the ultrasonic echo strain information, which is indicative of the determined level of tissue ablation.

12. The method of claim 11, wherein
    when the ultrasonic thermal ablation probe is the interstitial ablator, placing the ultrasonic thermal ablation probe in relation to the tissue region to be treated comprises inserting the interstitial ablator into a tissue, a natural cavity or a vessel in the tissue region, and
    when the ultrasonic thermal ablation probe is the external applicator, placing the ultrasonic thermal ablation probe in relation to the tissue region to be treated comprises contacting a surface of a tissue in the tissue region with the external applicator.

13. The method of claim 11, further comprising:
comparing the actual thermal dose profiles to a planned thermal dose profile; and
controlling of the power delivered by the ultrasonic thermal ablation probe is determined by the comparison of the actual thermal dose profiles to the planned thermal dose profile.

14. The method of claim 12, wherein the controlling comprises independently controlling intensity of a plurality of ultrasonic transducer elements provided on the ultrasonic thermal ablation probe.

15. The method of claim 11, wherein the monitoring comprises the use of a heat-induced strain algorithm.

16. The method of claim 15, wherein determining the level of tissue ablation comprises parallel implementation of the heat-induced strain algorithm.

17. The method of claim 16, wherein the parallel implementation of the heat-induced strain algorithm comprises:
dividing each line of radio frequency image data of an image captured by the ultrasonic three-dimensional imaging probe into pixels, the image having n lines of radio frequency image data and m pixels, and
performing separate parallel computations by running n blocks with m threads in each block.

18. The method of claim 17, wherein subsequent images captured by the ultrasonic three-dimensional imaging probe are compared using the parallel implementation of the heat-induced strain algorithm by aligning a number p of images, and performing separate parallel computations by running m blocks with (n×p) threads in each block.

* * * * *